United States Patent
Mortensen et al.

(10) Patent No.: US 10,292,638 B2
(45) Date of Patent: May 21, 2019

(54) APPARATUS FOR ELECTRICAL STIMULATION, IN PARTICULAR FOR BRUXISM

(75) Inventors: Troels Bierman Mortensen, Gentofte (DK); Claus Steen, Silkeborg (DK); Erling Rasmussen, Billund (DK); Morten Haugland, Svenstrup J (DK)

(73) Assignee: Sunstar Suisse SA, Etoy (CH)

( * ) Notice: Subject to any disclaimer, the term of this patent is extended or adjusted under 35 U.S.C. 154(b) by 1324 days.

(21) Appl. No.: 13/254,314

(22) PCT Filed: Mar. 4, 2010

(86) PCT No.: PCT/DK2010/050054
§ 371 (c)(1),
(2), (4) Date: Jun. 28, 2012

(87) PCT Pub. No.: WO2010/099796
PCT Pub. Date: Sep. 10, 2010

(65) Prior Publication Data
US 2012/0271190 A1 Oct. 25, 2012

Related U.S. Application Data

(60) Provisional application No. 61/181,332, filed on May 27, 2009, provisional application No. 61/181,343, (Continued)

(30) Foreign Application Priority Data

Mar. 4, 2009 (DK) .................. 2009 00289
Mar. 4, 2009 (DK) .................. 2009 00291
Mar. 4, 2009 (DK) .................. 2009 00292

(51) Int. Cl.
*A61B 5/00* (2006.01)
*A61B 5/0488* (2006.01)
(Continued)

(52) U.S. Cl.
CPC .......... *A61B 5/4557* (2013.01); *A61B 5/0488* (2013.01); *A61N 1/36014* (2013.01);
(Continued)

(58) Field of Classification Search
CPC ....................................... A61B 5/00
(Continued)

(56) References Cited

U.S. PATENT DOCUMENTS 4,669,477 A * 6/1987 Ober .................. A61N 1/36017
600/590
4,715,367 A * 12/1987 Crossley ................ A61B 5/113
600/27
(Continued)

FOREIGN PATENT DOCUMENTS

CN 1810319 A 8/2006
WO 0051543 A2 9/2000
(Continued)

*Primary Examiner* — May A Abouelela
(74) *Attorney, Agent, or Firm* — Dinsmore & Shohl LLP

(57) ABSTRACT

The present invention relates to a method and an apparatus for preventing, diagnosing, monitoring, and/or treating bruxism as well as related diseases of an individual. In a first aspect the invention relates to an apparatus for preventing bruxism of an individual, comprising: means for applying a plurality of stimulation signals for providing relaxation of at least one of the masticatory and/or facial muscles of said individual, means for applying said stimulations signals with a predefined setting, and means for applying said stimulations signals independent of activity of said muscle(s). The invention may be suitable for both nocturnal and awake bruxism.

16 Claims, 11 Drawing Sheets

Related U.S. Application Data filed on May 27, 2009, provisional application No. 61/181,346, filed on May 27, 2009.

(51) Int. Cl.
*A61N 1/36* (2006.01)
*A61F 5/56* (2006.01)
*A61N 1/04* (2006.01)

(52) U.S. Cl.
CPC .......... *A61B 5/4528* (2013.01); *A61B 5/4547* (2013.01); *A61B 5/7257* (2013.01); *A61F 2005/563* (2013.01); *A61N 1/0452* (2013.01)

(58) Field of Classification Search
USPC .............. 600/587, 595, 546, 544, 545, 300; 607/48; 128/905
See application file for complete search history.

(56) References Cited

U.S. PATENT DOCUMENTS

| | | | | |
|---|---|---|---|---|
| 4,838,283 A | * | 6/1989 | Lee, Jr. | A61F 5/566 128/859 |
| 4,989,616 A | * | 2/1991 | Lee, Jr. | A61B 7/001 128/859 |
| 4,995,404 A | * | 2/1991 | Nemir | A61B 5/224 600/590 |
| 5,265,624 A | * | 11/1993 | Bowman | A61B 5/113 128/848 |
| 5,540,733 A | * | 7/1996 | Testerman | A61B 5/1135 600/529 |
| 5,553,626 A | * | 9/1996 | Burger | A61F 5/566 600/587 |
| 5,766,124 A | * | 6/1998 | Polson | A61N 2/006 600/13 |
| 6,093,158 A | * | 7/2000 | Morris | A61B 5/11 600/590 |
| 6,270,466 B1 | | 8/2001 | Weinstein et al. | |
| 6,597,944 B1 | * | 7/2003 | Hadas | A61B 5/0488 60/587 |
| 6,638,241 B2 | * | 10/2003 | Yerushalmy | A61N 1/36014 600/590 |
| 8,016,776 B2 | * | 9/2011 | Bourget | A61B 5/0002 600/382 |
| 8,308,661 B2 | * | 11/2012 | Miesel | A61B 5/1116 600/544 |
| 8,579,794 B2 | * | 11/2013 | Henke | A61F 5/56 600/27 |
| 8,588,883 B2 | * | 11/2013 | Jadidi | A61B 5/0492 600/372 |
| 2004/0193068 A1 | * | 9/2004 | Burton | A61B 5/0476 600/544 |
| 2005/0076908 A1 | * | 4/2005 | Lee | A61B 5/0809 128/204.23 |
| 2005/0080463 A1 | * | 4/2005 | Stahmann | A61B 5/0488 607/62 |
| 2006/0184059 A1 | * | 8/2006 | Jadidi | A61B 5/04015 600/546 |
| 2008/0243023 A1 | * | 10/2008 | Valkhof | A61F 5/566 600/546 |
| 2010/0063350 A1 | * | 3/2010 | Henke | A61B 5/02055 600/28 |
| 2011/0105941 A1 | * | 5/2011 | Jadidi | A61B 5/0488 600/546 |
| 2011/0118581 A1 | * | 5/2011 | Jadidi | A61B 5/0492 600/372 |

FOREIGN PATENT DOCUMENTS

| | | |
|---|---|---|
| WO | 2003059160 A1 | 7/2003 |
| WO | 2004/087258 A1 | 10/2004 |
| WO | 2009035770 A3 | 6/2009 |

* cited by examiner

Pulse frequency = rate of pulses during a burst

Burst frequency = rate of bursts during a packet

Packet frequency = rate of packages during a period

APPARATUS FOR ELECTRICAL STIMULATION, IN PARTICULAR FOR BRUXISM

The present invention relates to a method and an apparatus for preventing, diagnosing, monitoring, and/or treating bruxism as well as related diseases of an individual.

BACKGROUND OF INVENTION

Bruxism is a condition characterised by powerful jaw movements without any real function and which takes the form of involuntary grinding movements of the teeth during strong clenching. This affliction may cause serious dental damages such as for example wearing of the teeth, damage to lips and the tongue, lose teeth, and gingival pockets. Bruxism is often in addition also associated with pain in the back of the head and chronic headache.

Chronic bruxism is divided into nocturnal and awake bruxism, where the latter is also denoted daytime bruxism. Awake bruxism is characterized by being a conscious clenching of upper and lower jaws and grinding of the teeth, although dominated by the latter. Since night-time bruxism is unconscious it may normally only be perceived by those in the surroundings (for example relations) as an unpleasant squeaky noise. Awake bruxism may often be provoked by exposure to stress. It may be relieved relatively easily by drawing the attention of the person to the bruxism. Night-time bruxism is often alleviated by protecting the teeth with a splint.

SUMMARY OF INVENTION

Attempts have been made to detect night time bruxism by the use of an electronic monitoring apparatus which provides a feedback or alarm signal when bruxism is detected. WO2004/087258 describes a sophisticated and effective form of such apparatus in which EMG (electromyography) signals are picked up from an electrode on the skin and are analysed electronically. The feedback signal is a stimulation signal sent back to the skin via the same electrodes. This signal is intended to be sufficient to have an effect on bruxism but not so strong as to wake the user.

In a first aspect, an object of the invention is to provide a more simple solution to prevent bruxism of an individual by applying a stimulation signal randomly in relation to any muscle activity. This is achieved by an apparatus for preventing bruxism of an individual, comprising:
  means for applying a plurality of stimulation signals for providing relaxation of at least one of the masticatory and/or facial muscles of said individual,
  means for applying said stimulations signals with a predefined setting, and
  means for applying said stimulations signals independent of activity of said muscle(s).

The invention furthermore relates to a method for preventing bruxism of an individual, comprising the steps of:
  applying a plurality of stimulation signals for relaxation of at least one of the masticatory and/or facial muscles of said individual,
  applying said stimulations signals with a predefined setting, and applying said stimulations signals independent of activity of said muscle(s).

The invention may be suitable for both nocturnal and awake bruxism.

To prevent bruxism it is crucial to provide relaxation of the muscles involved in the bruxism. These muscles are typically one or more of the masticatory and/or facial muscles. It is most common to stimulate the masseter and/or the temporal muscle. The stimulation signal applied to a muscle is provided to obtain subsequent relaxation of that muscle. In this aspect the stimulation signals are preferably applied independent of the state of any of the implicated muscles, i.e. in this aspect the stimulus is applied independent of whether the muscle is contracting or relaxed, i.e. independent of the individual contraction event. Furthermore, the apparatus may be adapted to apply the stimulation signals in one or more predefined periods during sleep if it is known that bruxism events are most likely in said period(s), see also below for a more detailed discussion of periods. Thus, in this embodiment of the invention monitoring of muscle activity is not provided. Thereby processing of monitoring signals is not necessary and a simple solution is provided.

Preferably at least one electrode assembly is provided for attaching to the skin of the individual for applying the stimulation signals.

In a preferred embodiment of the invention a stimulation signal is a pulse train with one or more of the following parameters being predefined: start current, end current, start voltage, end voltage, pulse width, pulse train duration, inter-pulse spacing, duty cycle (pulse), pulse set spacing, duty cycle (pulse set). One or more of the parameters can be pre-set as hardware defined parameters. Preferably an administrative user, a specialist, doctor, dentist or the like can define one or more of these parameters to fit the individual user of the apparatus. Preferably the user can define one or more of these parameters based on personal preference. See also below, wherein pulse set, pulse train, interpulse spacing, duty cycle etc. are discussed in details using preferred values.

In a preferred embodiment of the invention, said predefined setting comprises at least one frequency and/or at least one intensity of the applied stimulation signals. The frequency of the stimulation signals determines how often and when the stimulation signals are applied. The intensity of the stimulation signals are preferably determined by the user, e.g. during setup of the apparatus when the user can apply the stimulation signals at a range of different intensities and observe the effect of each intensity setting. Based on the user's individual preferences, the user can select a suitable intensity.

In one embodiment of the invention the intensity of the stimulation signals is defined by a current value. Furthermore, the intensity of the stimulation signals is preferably regulated by the current, i.e. current control. And by providing a current control to the regulation of the apparatus it is ensured that each stimulation signal will be provided with the correct predefined current value, i.e. each stimulation signal is provided with the predefined intensity and the electric shock applied to the user will thereby be the same and thereby felt similar as during setup. Preferred current values are discussed below.

The predefined settings may be determined by a specialist, an administrative user, the individual user and/or the like. In another embodiment at least a part of the settings are adapted automatically during use.

There may be more than one frequency relating to the stimulation signal. E.g. the stimulation signals, or a pulse train of stimulation signals, may be applied in packets. For example a packet of stimulation signals may be applied every minute for a period of time or every 30 seconds, or every 20 seconds. The packet of stimulation signals may have an internal frequency, e.g. within a packet the stimulation signals are applied once every second for ten seconds. FIG. 3 shows a graphic presentation of pulses and packets in a period. The pulse frequency is the rate of pulses during a burst, and the burst frequency is the rate of bursts during a packet. The packet frequency is then the rate of packages during a period. The period may for example be the whole sleep period, or the periods during sleep for which it is experienced that the bruxism events are most likely to occur. FIG. 9 shows consecutive waves of non-REM-to-REM (solid horizontal boxes) sleep cycles (I to IV). During the first third of the night, slow-wave sleep (stages 3 and 4) is dominant. During the last third of the night, the REM stage is longer. (MT movement time, WT wake time) (Adapted from Lavigne et al with permission). FIG. 10 shows that the grinds per hour varies with the sleep cycles. Accordingly, a period may be the part of a sleep cycle having increased grinding events.

In one embodiment of the invention the stimulation signals, also denoted pulses, are provided randomly and/or can be provided randomly, such as randomly distributed over at least one period of time.

In one embodiment of the invention the stimulation signals over a period of time are applied with a frequency of 0.00001-100 Hz, such as 0.00001-0.0001 Hz, 0.0001-0.001 Hz, 0.001-0.01 HZ, 0.1-1 Hz, 1-5 Hz, 5-10 Hz and/or 10-100 Hz.

In one embodiment of the invention the apparatus comprises a housing and electrodes, with the electrodes preferably mounted on one side of the housing. Preferably the housing has a width and/or length which is substantially larger than the height, such as at least 2, 3, 4, 5, 6, 7 or 8 times the height. The height of the housing is the height measured perpendicular to the skin when attached to the skin of an individual.

The entire device may thus have a height of less than 20 mm, such as less than 15 mm, such as less than 12 mm, such as less than 10 mm, such as less than 8 mm, such as less than 7 mm, such as less than 6 mm, such as less than 5 mm, such as less than 4 mm, such as less than 3 mm, less than 2 mm, such as less than 1 mm. The device may be flexible to provide optimal comfort for the user.

The length of the housing may be 20 mm to 100 mm, such as 30 to 90 mm, such as 40 to 80 mm, such as 50 to 70 mm. The length of the housing covers the extension of all the electrodes.

The width of the housing may be 10 to 60 mm, such as 20 to 50 mm, such as 30 to 40 mm.

In one embodiment the housing accommodates at least one battery and the necessary electronics. The housing may also comprise an interface to e.g. a main terminal or a PC for changing the setting of the apparatus, recharging the battery and the like. Connection with a main terminal or the PC may be wireless. See also FIG. 13 and Example 6 for further details.

Combination Apparatus

In a second aspect of the invention the apparatus further comprises means for monitoring signals indicative of bruxism, means for processing of said signals in order to detect bruxism, and means for providing a feedback signal in response to detection of bruxism. Thus, this embodiment is a combination of features where stimulation signals can be provided independent of muscle activity but stimulation signals may also be provided when bruxism is detected. In this case the stimulation signals will be feedback signals, because they are applied as a result of a specific muscle activity. An example according to this aspect is a device as shown in WO2004/087258 further comprising means as defined above for providing stimulation signals independent of muscle activity.

Another aspect of the invention relates to a kit with bruxism monitoring (and/or treatment) combined with a standalone miniature device.

Adaptation to Bruxism Events

The extent of bruxism may vary greatly from person to person in terms of frequency, intensity and duration and also in terms of outcome and impact of the bruxism, e.g. diseases, pain, sufferings and malfunctions as a direct or indirect result of bruxism.

There may also be differences in how individuals experience and react to the stimulation signals, both conscious and unconscious, physically and mentally. Therefore a further aspect of the invention relates to individually adapting the stimulation signals applied to an individual based on monitored muscle activity signals. Preferably also based on how the individual adapts to the applied stimulation signals, i.e. the stimulation signals may be continuously optimised. In one embodiment of the invention the frequency and/or intensity of the applied stimulation signals are adjusted in response to intensity, impact, frequency and/or duration of detected bruxism episodes. Thus, the settings of the stimulation signals that are provided independent of muscle activity may be adapted to an actual detected bruxism pattern and/or adaptive intelligent calculations based on detected muscle activity. For example the apparatus may be self-adaptive, e.g. by means of pattern recognition, to address a bruxism event before the actual event, i.e. muscle activity may show a certain pattern before bruxism begins, and preferably the apparatus may provide recognition of said pattern and stimulate and relax the muscles before bruxism begins. There may for example prior to bruxism be an increased tension in the muscle, certain characteristic frequencies or spikes in the muscle activity signals and/or the like. In known anti-bruxism devices biofeedback is provided when a certain muscle activity intensity threshold is reached, i.e. typically after bruxism has begun.

Treatment

A third aspect of the invention relates to a method for treatment of one or more of the following disorders: bruxism, awake bruxism, chronic bruxism, night time bruxism, dental wear, temporal mandibular joint disease (TMJ), tinnitus, migraine, headache, tension headache, preferably by means of any of the listed apparatuses.

Adaptation to Changes in Skin-Electrode Connection

A fourth aspect of the invention relates to a stimulation apparatus that adapts to changes in skin-electrode connection. The apparatus may be an apparatus applying signals independent of muscle activity or an apparatus using feedback stimulus as well as a combination apparatus as discussed above.

The stimulation signal corresponds to a mild electric shock provided to the user. A voltage is applied between two or more electrodes and the actual stimulation/shock felt by the user is determined by the amount of current transferred via the skin between the electrodes. The amount of current will depend on the connection between skin and electrodes, i.e. poor connection may result in higher resistance providing a lower flow of current for the same voltage. However, a better skin-electrode connection, possibly due to perspiration, may result in a higher flow of current and thus an increased electrical shock applied to the user.

An object of the invention is therefore to provide a muscle stimulation apparatus that adapts to changes in the skin-electrode connection. This is provided by an apparatus for providing a plurality of current controlled electrical stimulation signals to at least one of the masticatory and/or facial muscles of an individual, said apparatus comprising:
- at least one electrode assembly for applying the stimulation signals to the skin of the individual,
- means for defining the intensity of the stimulation signals by a current value, and
- means for adapting to change in the skin-electrode contact by means of regulating the stimulation signals by the current.

The invention furthermore relates to a method for providing a plurality of current controlled electrical stimulation signals to at least one of the masticatory and/or facial muscles of an individual, said method comprising the steps of:
- defining the intensity of the stimulation signals by a current value,
- applying the stimulation signals to the skin of the individual by means of at least one electrode assembly, and
- adapting to change in the skin-electrode contact by means of regulating the stimulation signals by the current.

By adapting to change in the conditions the stimulation signals will be more consistent and thereby more pleasant to the user (i.e. the individual). The intensity of the stimulation signals are preferably determined by the user, e.g. during setup of the apparatus when the user can apply the stimulation signals at a range of different intensities and observe the effect of the electric shock felt at each intensity setting. Based on the user's individual preferences, the user can select a suitable intensity.

This intensity is preferably defined by a current value. And by providing a current control to the regulation of the apparatus it is ensured that each stimulation signal will be provided with the correct predefined current value, i.e. each stimulation signal is provided with the predefined intensity, and the electric shock applied to the user will thereby be the same and thereby felt similar as during setup.

If the skin-electrode conditions change during use of the apparatus the current controlled stimulation signals will provide for an automatic adaptation to the changing conditions. For example a better skin-electrode connection, i.e. lower impedance between electrodes, will provide for a lower applied voltage between the electrodes to provide for the correct current in the stimulation signal.

In a fifth aspect of the invention the apparatus comprises more than one electrode assembly. Preferably the stimulation signals to each electrode assembly are current controlled. Preferably the intensity of the stimulation signal applied to each electrode assembly can be defined independently.

In a sixth aspect of the invention the apparatus further comprises
- means for providing supervisory signals indicative of muscle activity relating to bruxism of said individual by means of at least one electrode assembly,
- means for processing said supervisory signals in order to detect bruxism, and
- means for providing a current controlled electrical stimulation signal in response to detecting bruxism.

A seventh aspect of the invention relates to monitoring the skin-electrode contact by continuously monitoring the impedance between the electrodes in the electrode assembly by means of an embedded monitoring signal.

The current of a stimulation signal may be least 0.5 mA, such as at least 1.0 mA, such as at least 1.5 mA, such as at least 2.0 mA, such as at least 2.5 mA, such as at least 5.0 mA, such as at least 7.5 mA, such as at least 10.0 mA, such as at least 12.5 mA, such as at least 15.0 mA, such as at least 17.5 mA, such as at least 20.0 mA, such as between 0 and 7 mA, such as between 1 and 7 mA.

The apparatus according to the invention is preferably current controlled, however for practical reasons a certain degree of voltage control may be necessary. Thus in further embodiments of the invention a stimulation signal is 50-100% current controlled and 0-50% voltage controlled, such as 50% current controlled and 50% voltage controlled, such as 55% current controlled and 45% voltage controlled, such as 60% current controlled and 40% voltage controlled, such as 65% current controlled and 35% voltage controlled, such as 70% current controlled and 30% voltage controlled, such as 75% current controlled and 25% voltage controlled, such as 80% current controlled and 20% voltage controlled, such as 85% current controlled and 15% voltage controlled, such as 90% current controlled and 10% voltage controlled, such as 95% current controlled and 5% voltage controlled, such as 99% current controlled and 1% voltage controlled, such as 100% current controlled and 0% voltage controlled.

FIG. 1 is a graphic representation of the current applied during a stimulus depending on the contact resistance, ie. resistance between the skin and the electrode. The line ------ shows the current applied during a 100% current controlled apparatus, whereas the line ...... shows the current applied during a 100% voltage controlled apparatus. The line _____ (Grindcare) shows the current applied when a degree of voltage control is included, in the present example the stimulation signal is about 80-90% current controlled and 10-20% voltage controlled.

In a further embodiment of the invention the electrode assembly comprises more than one electrode.

In a further aspect of the invention the at least one electrode assembly can be applied to the skin of the individual at various positions of the head, such as at or near to the following anatomical regions: temple, forehead, cheek, mandible, maxillary jaw, nose, neck, mouth, ear, and/or the like.

Monitoring Anatomical Location of Muscular Activity

An eight aspect embodiment of the invention relates to monitoring anatomical location of muscular activity related to bruxism of an individual and comprises:
- means for providing signals indicative of muscle activity related to bruxism by means of a plurality of electrode assemblies applied to various facial positions of the individual,
  or,
- means for providing signals indicative of muscle activity related to bruxism by means of one electrode assembly applied to various facial locations of the individual over a period of time, and
- means for processing said signals in order to detect bruxism and provide a facial map of bruxism activity.

Yet a further embodiment of the invention comprises:
- means for monitoring bruxism of the individual over one or more periods of time, such as more than one night such as every night of a week,
- means for collecting and storing bruxism data for each period of time,
- means for processing bruxism data for analysis of impact of bruxism for each period of time, and
- means for presenting bruxism impact vs. period of time and/or bruxism impact vs. facial location.

Another aspect of the invention relates to customised and/or individually adapted and/or individually adjusted muscular stimulation signals provided to different facial locations dependent on local occurrence and/or impact of bruxism.

Determination of Impact of Bruxism

A bruxism event may last from few ms to half a minute, and the force exerted by the muscles may vary greatly. The effect of a bruxism event may vary depending on both the length of the event and the force exerted by the muscles and/or absorbed in jaw and teeth, and accordingly, the impact of bruxism is multidimensional, wherein the intensity and time of each event is included, as well as the more subjective symptoms, such as the pain felt by the individual. Thus, an object of the invention is to be able to estimate the impact of bruxism, preferably to be able to assess the extent of bruxism over a period of time, such as during a night.

A ninth aspect of the invention relates to an apparatus for determining the impact and/or extent of bruxism of an individual for a period of time, said apparatus comprising:
means for monitoring muscle activity signals of at least one of the masticatory and/or facial muscles,
means for processing/analysing said signals in order to determine the duration and intensity of each bruxism episode and to count the number of bruxism episodes,
means for determining the total impact of bruxism for said period of time,
means for displaying the result(s) of the impact.

The invention further relates to a method for determining the impact and/or extent of bruxism for a period of time of an individual, said method comprising the steps of:
measuring muscle activity signals of at least one of the masticatory and/or facial muscles,
processing/analysing said signals in order to determine the duration and intensity of each bruxism episode and to count the number of bruxism episodes,
determining the total impact of bruxism for said period of time by combining the results obtained in step b), and displaying the result(s) of the impact.

The "impact" of bruxism can be impact to for example teeth, jaw, muscles, joints, scull and the like.

In a preferred embodiment of the invention the impact of bruxism is determined by means of integrating the intensity vs. time for each bruxism episode, i.e. to integrate the length-force diagram. Preferably the apparatus according to the invention comprises means for storing the muscle activity signals and/or the result(s) of the impact.

Preferably a bruxism event may be characterised as muscle activity above a certain threshold. This is described in WO2004/087258. The value of this threshold can be defined in terms of intensity, duration, strength, voltage, (biting) force and/or the like, and the threshold can be predetermined and/or determined during a setup phase by the user and/or a specialist. See also Examples 2 and 3, and related figures.

In terms of determining the abovementioned impact a solution may be to integrate the total muscular activity intensity vs. time. Thus every detected muscle activity is part of the integration. However, muscle activity in one of the masticatory or facial muscles may not necessarily be an indication of bruxism. And the determined impact may therefore not provide a true measure of the extent of bruxism. Another solution is to only include muscular activity intensity above a predefined threshold in the integration procedure. However, if the threshold has been incorrectly defined there is a risk of underestimating the impact of bruxism. In one embodiment of the invention the total muscular intensity vs. time and the muscular activity intensity above a predefined threshold is integrated thereby providing both the total impact and the specifically impact of events above the threshold.

Preferably the muscle activity signals are monitored by means of at least one electrode assembly, preferably an EMG electrode assembly.

In one embodiment of the invention a feedback signal to the at least one masticatory and/or facial muscle can be provided in response to detecting a bruxism event. This feedback signal is provided to reduce the muscle activity and thereby stop the bruxism. The feedback signal combined with the determination of the impact of bruxism provides a user of the apparatus with the option of being able to monitor the result of providing the feedback signal, e.g. during night. If the feedback signals provide relaxation of the relevant muscles when bruxism is detected, the impact of bruxism should decrease over time and the user will be able to monitor the progress on the apparatus.

A result of bruxism can be dental wear and by determining the impact of bruxism a measure of dental wear may thereby be provided. Thus, one aspect of the invention relates to estimate and/or asses and/or measure the dental wear of the individual based on the determined impact of bruxism. A further aspect of the invention relates to determining the dental wear of local areas of the set of teeth or a denture, such as dental wear of right and/or left side, the mandible, the maxillary, front, back, central, molar and/or the like. Evaluating impact of bruxism and assessing local differences in dental wear relates to analysing muscle activity from different parts of the face. This can e.g. be provided by using one electrode assembly that can be attached to different parts of the head and separately measuring, analysing and comparing muscle activity from said different parts of the face, thereby obtaining a "facial map" of the muscle activity. In a further aspect multiple electrode assemblies are provided, such as at least two, three, four, five, six, seven, eight, nine or at least ten electrode assemblies, to be attached to different parts of the head concurrently. Analysing muscle activity signals from different parts of the head may provide a "facial map" of the muscle activity.

A further aspect of the invention relates to an electrode assembly comprising multiple electrodes, such as at least two, three, four, five, six, seven, eight, nine or at least ten electrodes, to provide electrode attachment to multiple locations concurrently.

Bruxism may cause severe damage to the teeth and dental restoration may be necessary as a result of bruxism. However, dental restoration/implants may be even more fragile than natural teeth. Thus, providing a dental restoration of an individual suffering from bruxism will only postpone the problem. Therefore a further aspect of the invention relates to a method for screening and/or risk assessment of an individual prior to dental restoration and/or dental implant operation by determining the impact of bruxism for a period of time, such as a night, week or month, for said individual thereby evaluating the total and/or the local (left, right, molar, premolar, canine, incisor) dental wear, and/or the necessary strength and/or type of the dental implant. In general the method can be applied to individuals prior to any dental changes. The dentist can maybe see a certain wear of the teeth, possibly due to teeth grinding. However, it may be difficult to assess any impact to the teeth solely based on the dental wear. Therefore the individual may be asked to use the apparatus for a period of time, such as every night for one or more weeks. This may be provided in monitoring mode only, i.e. without any feedback signals if bruxism is detected. The dentist may then evaluate the recorded impact of the apparatus and based on that determine whether a dental work can be safely practised without risk of future damages due to teeth clenching. If the impact of bruxism of an individual is determined as too high for a safe dental restoration, the individual may be asked to use the apparatus for an additional period of time, this time providing feedback signals in response to detected teeth grinding. After the additional period of time the impact can be evaluated again.

The apparatus may also be provided to an individual after a dental restoration procedure to be sure that no teeth grinding will occur while the teeth are sensitive due to the dental procedure.

The measured impact of bruxism is a value or an indication provided by the apparatus. However the user may have a different perception and/or a personal opinion of the course of events. A further embodiment of the invention therefore comprises means for entering at least one value representing the individual's personal perception of pain and/or tenderness of the jaw and/or masticatory muscles and/or facial muscles on a psychometric response scale, such as a visual analogue scale (VAS), and wherein said at least one value is stored. Thereby the determined impact of bruxism can be evaluated against the user's individual opinion. When responding to a VAS item, respondents specify their level of agreement to a statement by indicating a position along a continuous line between two end-points.

The data analysed, processed and/or stored by the apparatus according to the invention can be presented in various ways. Preferably the displaying means of the apparatus comprises graphical and/or numerical displaying of one or more of the following parameters: the total impact of bruxism, the average and/or median impact, duration, strength and/or biting force of each bruxism episode, the number of bruxism episodes, the number of bruxism episodes above a predefined (biting force) threshold, the progression of the impact during one or more periods of time, a long term evaluation of bruxism impact, short term and long term comparison with personal perception of pain and tenderness.

Electrodes

In one embodiment of the invention the electrode assembly comprises three electrodes in a fixed spatial relationship one to another, each electrode having a contact area for electrical connection with the skin which is spaced from the contact area of each other electrode in the electrode assembly by at least 2 mm, the maximum distance from an edge of one electrode contact area to the furthest edge of the furthest away of the other electrode contact areas being not greater than 60 mm.

The electrodes may be mounted on a common substrate. It will be appreciated that the electrodes may each comprise a solid conductive electrode member provided with a respective patch of conductive gel in said assembly, in which case it will be the area of the gel that defines the contact area of the electrode rather than the size of the electrode member.

The area of an electrode member in contact with such a gel patch may be approximately from 5% to 100% of the electrode contact area (i.e. the gel patch area), in some cases 25% to 75%, e.g. about 50%.

In one embodiment the electrodes are provided to fit well along the front edge of the temporal muscle. The electrodes may be arranged to lie on a line which is a straight line. However, in order to match the shape of the temporal muscle near the temple of the patient the electrodes may be arranged to lie on a line which is an arc of a circle having a radius of from 50 mm or more. Preferably, such a circle has a radius of 60 mm or more, such as from 60-200 mm, for instance about 70 mm. Preferably, centres of the contact areas of such electrodes lie on such lines. Thus, the electrodes may be arranged such that centres of said electrodes and of the electrode contact areas and/or of the electrode members lie on a line which is an arc of a circle having a radius of from 50-500 mm, more preferably from 60-200 mm, e.g. about 70 mm.

The electrode contact areas may extend along or on a said line a distance of from 1 to 10 mm from one side to an opposite side of the electrode contact area and may extend transversely of a said line by a distance of from 1 to 10 mm from one side to an opposite side of the electrode contact area, the maximum distance along said line from an edge of a first said electrode contact area to an opposite edge of the furthest away of the other two electrode contact areas being not more than 60 mm, more preferably 50 mm. Preferably, the contact areas of the electrodes may extend along or on said line a distance of from 3 to 7 mm from one side to an opposite side of the electrode contact area. Similarly, the contact areas of the electrodes may extend transversely of said line by a distance of from 3 to 7 mm from one side to an opposite side of the electrode contact area.

Thus, for instance the electrode contact areas may be circular and of diameter from 2-20 mm, more preferably from 5-15 mm, e.g. about 10 mm, and the electrode members may also be circular having a diameter of from 1-10 mm, more preferably from 3 to 7 mm, e.g. about 5 mm. The electrode contact areas and the electrode members may be of other shapes having equivalent areas to those described above.

Preferably, the maximum distance along said line from an edge of a first said electrode contact area to an opposite edge of the furthest away of the other two electrode contact areas is from 20 to 50 mm, more preferably from 30 to 50 mm, e.g. about 40 mm.

Whilst the generally linear configuration of the electrodes is preferred, optionally the contact areas of the electrodes may be arranged in a triangular arrangement in which the longest side of the triangle so defined is not more than 40 mm, more preferably not more than 30 mm.

The frequency content of the received signals is preferably analysed by Fourier analysis, suitably using a DFT (Digital Fourier Transform), particularly an FFT (Fast Fourier Transform) signal analysis. This can produce a power spectrum from which specific frequency bands may be selected to form the basis of the measurement.

It is furthermore an object of the invention to provide that the apparatus can distinguish between muscle activity due to bruxism and normal muscle activity. In one embodiment of the invention this is achieved by letting said apparatus be operable in a set-up mode and in a use mode. In said set-up mode the apparatus is configured to accept an input defining said at least one predetermined frequency and in said use-mode the apparatus detects bruxism episodes by measuring the amplitude of muscle activity signals at least one frequency received from said electrode assembly.

In order to determine for a given user the ideal frequency or frequencies to measure so as reliably to determine the occurrence of a bruxism episode, it is preferred that said apparatus is operable in said set-up mode to measure a first power spectrum of signals received from said electrode assembly when a user carries out a first exercise simulating bruxism muscle activity (such as teeth clenching) and to measure a second power spectrum of signals received from said electrode assembly when a user carries out a second exercise simulating muscle activity from which bruxism muscle activity is to be distinguished (such as grimacing), and is operable to display said first and second power spectra to allow a user to identify one or more frequencies that differ strongly between said power spectra for use as said predetermined frequencies. The power spectra may be produced by FFT analysis as described above.

In a further embodiment of the invention the apparatus is operable in said set-up mode to measure a first power spectrum of signals received from said electrode assembly when a user carries out a first exercise simulating bruxism muscle activity and to measure a second and/or a third power spectrum of signals received from said electrode assembly when a user carries out a second and/or a third exercise simulating muscle activity from which bruxism muscle activity is to be distinguished. In one embodiment of the invention the second exercise is normal muscle activity such as grimacing. In yet another embodiment the third exercise is when a user when carries out substantially no muscle activity. Furthermore, the device is operable to display said first, second and/or third power spectra to allow a user to identify at least one frequency that differ strongly between said power spectra for use as said predetermined frequencies.

The set-up process may be automated if it is arranged that said apparatus by means of machine computation provides for:
    identification of at least one frequency that differ strongly between said power spectra for use as said predetermined frequencies, and
    input of at least one of said frequencies for use in said use-mode.

The apparatus may also be configured such that in said set-up mode it registers received signals produced when the user makes no facial movement and establishes therefrom a value of the amplitude at the frequency or frequencies used for bruxism determination that corresponds essentially to noise rather than any significant muscle activity.

Thus, it may be determined that an episode of bruxism is occurring, and a stimulation signal may be triggered, if a sufficiently large amplitude (A) is measured at a frequency or band of frequencies selected over and above the noise value recorded as above at the selected frequency or frequency band. This may be expressed such that an episode of bruxism is detected if a sufficiently large value of Y is produced according to the formula:

$(A-N)*S>Y;$

Where:
A=Measured Amplitude at the given frequency
N=Measured Noise at the given frequency
S=Sensitivity The value of 'S' may be adjusted in the set-up to suit an individual user, as may the threshold value of 'Y' above which bruxism is considered to be occurring.

More preferably, a double condition is required to be satisfied, such that:

$(A_{f1}-N_{f1})*S_{f1}>Y_{f1}$ and $(A_{f2}-N_{f2})*S_{f2}>Y_{f2}$ at the same time, where the subscripts 'f1' and 'f2' respectively indicate values of A, N, S and Y at a first frequency or band of frequencies and a second frequency or band of frequencies, separate from or overlapping with the first. Each frequency or frequency band may be identified by the user or an expert or by automatic machine computation as best reflecting differences in the power spectra of signals received in set-up mode from bruxism simulation as by teeth clenching on the one hand and the generation of potentially confounding signals as by grimacing on the other hand.

In a further embodiment of the invention the signal processing means conducts a Fourier transform analysis of said signals to determine the amplitude in said signals at a first frequency or band of frequencies and a second frequency or band of frequencies, separate from or overlapping with the first.

A further object of the invention is to provide that the stimulation signal has the desired effect on bruxism behaviour, for example enough power to have an impact on the temporal muscle. However it is important that the user is not disturbed or wakened from sleep. Preferably the stimulation signal is adjustable to achieve these ends. Therefore a match is needed between the form of the signal and the form of the electrode assembly. For use with the electrode assembly conformations described herein, it is preferred that said electrical stimulation signal is a biphasic signal which is initiated at a voltage applied to the electrode assembly of not more than 10 volts peak to peak and is raised to a maximum peak to peak voltage at a rate of not more than 500 V/sec, said signal having a duration of not more than 2 sec, a said maximum voltage of not more than 100 volts peak to peak.

Preferably, said biphasic signal has a pulse width of from 50 μsec to 10 msec, more preferably from 50 to 500 μsec, more preferably from 100 to 300 μsec, for instance about 150 μsec.

The signal is preferably initiated at a voltage applied to the electrode assembly of not more than 5 volts peak to peak. The signal preferably increases in intensity from its initial value at a rate of not more than 350 V/sec, more preferably not more than 250 V/sec, for instance between 100 and 250 V/sec, e.g. about 200V/sec. The duty cycle of the signal may be from 1 to 99%, but is preferably in the range of from 30 to 70%, suitably about 50%.

The form of the stimulation pulse should be tailored to suit the size and layout of the electrodes. An example of pulse train is the following: The pulses start gently, so as to avoid a sudden shock which might awaken the user, suitably starting from zero volts as shown, see also the graphic presentation in FIG. 3. The parameters of a pulse train could be as follows:

| | |
|---|---|
| Start voltage = | 0 V (peak-peak) |
| End voltage = | 76 V (peak-peak) |
| Pulse width = | 250 μsec |
| Pulse train duration = | 400 msec |
| Inter-pulse spacing = | 250 μsec |
| Duty cycle (pulse) = | 50% |
| Pulse set spacing = | 5 msec |
| Duty cycle (pulse set) = | 10% |

In this specific embodiment of the apparatus each individual pulse within the stimulation pulse has a duration of 250 μsec and positive voltage pulses of that duration alternate with negative voltage pulses of the same duration. There is a pause between positive and negative pulses of 250 μsec, producing a duty cycle of 50%. An example of a pulse cycle is shown in FIG. 2.

One embodiment of the apparatus according to the invention is powered by a small battery, the output from which is chopped and transformed to high voltage and is stored in high voltage capacitors. A complete stimulation cycle typically comprises about 80 pulse cycles, positive and negative pulses spaced by a pause making up each pulse cycle. The pulse cycles slowly increase in intensity up to a programmed current value. Between each pulse cycle, the energy for the next pulse cycle is pumped to the high voltage capacitors.

In one embodiment of the connection of the electrodes to the skin is monitored at frequent intervals and the application of the stimulation is blocked if no sufficient connection is present. The processor shown in FIG. 13 carries out FFT analysis of the signals received from the electrode assembly so as to produce a power spectrum therefrom. In a set-up mode, signals may be registered that arise from the user being relaxed (without significant activity of the temporal muscle), then with the user making deliberate facial muscle activities such as may be produced in grimacing which need to be distinguished in the use of the apparatus from signals produced in bruxism, and then with the user simulating bruxism by clenching their teeth strongly. From the FFT analysis of the signals produced by grimacing compared to those produced by clenching, frequencies may be identified either by user or expert inspection of the power spectra or automatically in the apparatus that strongly differentiate these activities for the individual user. Alternatively however, the apparatus may be pre-programmed to use frequencies that work well for most users.

Signals received when the user is relaxed may be used to establish a noise value at the relevant frequencies, which may be taken into account in determining in the use mode whether there is a sufficient amplitude detected to indicate bruxism.

Exteroceptive Suppression Period

A ninth aspect of the invention relates to the exteroceptive suppression period (ESP) (sometimes also referred to as the masseter silent period (MSP) or the masseter inhibitory reflex). The ESP is a reflex that results in relaxation of the jaw, e.g. the masseter and temporalis muscles. It is well known that ESP can be evoked by stimulation of the face, such as mechanical, heat or electrical stimulation, and it is known that there is a stimulation threshold for evoking the ESP, i.e. the ESP is evoked above a certain stimulus threshold. This threshold varies between individuals. Thus, it is a further object of the invention to address issues relating to ESP and bruxism.

This is provided by a method for treating bruxism, said method comprising applying a stimulus to the facial region, wherein the stimulus is sufficient for inducing an Exteroceptive Suppression Period (ESP) for the muscle(s) involved in bruxism.

This method preferably applies to both nocturnal and awake bruxism.

A further aspect of the invention relates to the frequency of the pulses and/or the pause between the pulses that is necessary to continuously evoke and/or induce the ESP of an individual, for example when the individual is sleeping but possibly also during the day. With a continuously induced ESP the jaw may be kept in a more or less permanent relaxed condition. How to continuously induce the ESP depends on the duration of the early (ES1) and/or the late (ES2) ESP and will vary from person to person.

In a further aspect of the invention the stimulus is a stimulus having no impact on brain activity, such as a stimulus selected from a tactile stimulus, a temperature stimulus and an electric stimulus. Typically a stimulus having no impact on brain activity, or rather cortical activity, is a stimulus that has no impact on sleep as discussed in Example 4.

In a further embodiment of the invention the stimulus is an electric stimulus having a current of at least 0.5 mA, such as at least 1.0 mA, such as at least 1.5 mA, such as at least 2.0 mA, such as at least 2.5 mA, such as at least 5.0 mA, such as at least 7.5 mA, such as at least 10.0 mA, such as at least 12.5 mA, such as at least 15.0 mA, such as at least 17.5 mA, such as at least 20.0 mA, such as between 0 and 7 mA, such as between 1 and 8 mA.

The stimulus may be one electric pulse and/or the stimulus may be a train of pulses, such as at least 5 pulses, such as at least 10 pulses, such as at least 15 pulses, such as at least 20 pulses, such as at least 25 pulses, such as at least 50 pulses, such as at least 75 pulses.

The duration of the train of pulses may be at least 10 msec, such as at least 20 msec, such as at least 50 msec, such as at least 100 msec, such as at least 200 msec, such as at least 300 msec, such as at least 400 msec, such as at least 500 msec, such as at least 600 msec, such as at least 700 msec, such as at least 800 msec, such as at least 1 second.

The intensity of the pulse may be increased during the train of pulses and/or the intensity of the pulse decreases towards to end of the train of pulses.

The duration of each pulse may be at least 50 microsec, such as at least 100 microsec, such as at least 150 microsec, such as at least 200 microsec, such as at least 250 microsec.

The start voltage (peak to peak) and the end voltage can be between 0 and 100 V, such as at least 0.1 V, such as at least 0.5 V, such as at least 1 V, such as at least 2.5 V, such as at least 5 V, such as at least 10 V, such as at least 20 V, such as at least 30 V, such as at least 40 V, such as at least 50 V, such as at least 60 V, such as at least 70 V, such as at least 80 V, such as at least 90 V.

The inter pulse spacing and/or the pulse set spacing can be between 0 and 100 milliseconds (ms), such as between 0 and 50 ms, such as between 0 and 25 ms, such as between 0 and 10 s, such as between 0 and 5 ms, such as between 0 and 2.5 ms, such as between 0 and 1 ms, such as between 0 and 500 microseconds (μs), such as between 0 and 400 μs, such as between 0 and 300 μs, such as between 0 and 200 μs, such as between 0 and 100 μs, such as between 0 and 50 μs, such as between 0 and 25 μs, such as between 0 and 10 μs, such as between 0 and 5 μs, such as between 0 and 1 μs, such as between 100 and 200 μs, such as between 200 and 300 μs, such as between 300 and 400 μs.

The duty cycle of the pulse and/or the duty cycle of the pulse set can be between 0 and 100%, such as between 0 and 10%, such as between 10 and 20%, such as between 20 and 30%, such as between 30 and 40%, such as between 40 and 50%, such as between 50 and 60%, such as between 60 and 70%, such as between 70 and 80%, such as between 80 and 90%, such as between 90 and 100%.

As an example a pulse train can have the following characteristics:

| | |
|---|---|
| Start voltage = | 0 V (peak-peak) |
| End voltage = | 76 V (peak-peak) |
| Pulse width = | 250 μsec |
| Pulse train duration = | 400 msec |
| Inter-pulse spacing = | 250 μsec |
| Duty cycle (pulse) = | 50% |
| Pulse set spacing = | 5 msec |
| Duty cycle (pulse set) = | 10% |

The frequency of the applied pulse trains can be 0.00001-100 Hz, such as 0.00001-0.0001 Hz, 0.0001-0.001 Hz, 0.001-0.01 HZ, 0.1-1 Hz, 1-5 Hz, 5-10 Hz and/or 10-100 Hz.

Induction of ESP can be depending on the energy of the applied pulse and/or pulse train that can be between 0 and 10 J, such as between 0 and 5 J, such as between 0 and 2 J, such as between 0 and 1 J, such as between 0 and 0.5 J, such as between 0 and 0.3 J, such as between 0 and 0.25 J, such as between 0 and 0.2 J, such as between 0 and 0.15 J, such as between 0 and 0.1 J, such as between 0 and 0.05 J, such as between 0 and 0.025 J, such as between 0 and 0.01 J, such as between 0 and 0.001 J.

In a further embodiment of the invention the pulse settings are adapted to ES1 (early ESP) and/or ES2 (late ESP).

How to induce and/or evoke the ESP may vary greatly between individuals. A further object of the invention therefore relates to individual adaptation of the stimulation signal to most efficiently induce and/or evoke the ESP of an individual, preferably by means of adapting the stimulation signals based on monitored muscle activity signals. E.g. analysing the pattern of the muscle activity signals in terms of frequency, amplitude, intensity, occurrence of various characteristics, and/or the like. Possibly also monitoring muscle activity from several locations of the head concurrently. Preferably the adaptation is also based on how the individual adapts to the applied stimulation signals, e.g. in terms of the response to a stimulation signals as a function of intensity, frequency, delay, current, shape of pulse and/or pulse train, pulse width, duty cycle, inter pulse spacing, ramping of the pulse(s) and/or the like. Thus the stimulation signals may be continuously optimised to better induce and/or evoke the ESP, e.g. to obtain the fastest response and/or the most prolonged effect of the reflex.

Evoking and/or inducing the ESP of an individual may provide a method for treatment of diseases like TMD, TMJ, migraine and headache.

In a further aspect of the invention any of the listed apparatuses may be applied to any of the listed methods for treating bruxism wherein an exteroceptive suppression period for the muscle(s) involved in bruxism is induced.

DESCRIPTION OF DRAWINGS

The invention will now be described in greater detail in which.

EXAMPLES

Example 1—Concordance

Bruxism events were detected on an apparatus according to the invention and furthermore, bruxism events or grinds were detected according to the "golden standard", namely as described in the scientific article: G. J. Lavigne, P. H. Rompre, J. Y. Montplaisir "Sleep Bruxism: Validity of Clinical Research Diagnostic Criteria in a Controlled Polysomnographic Study" Journal of Dental Research, vol. 75(1): pp. 546-552, January, 1996

Figure 1:
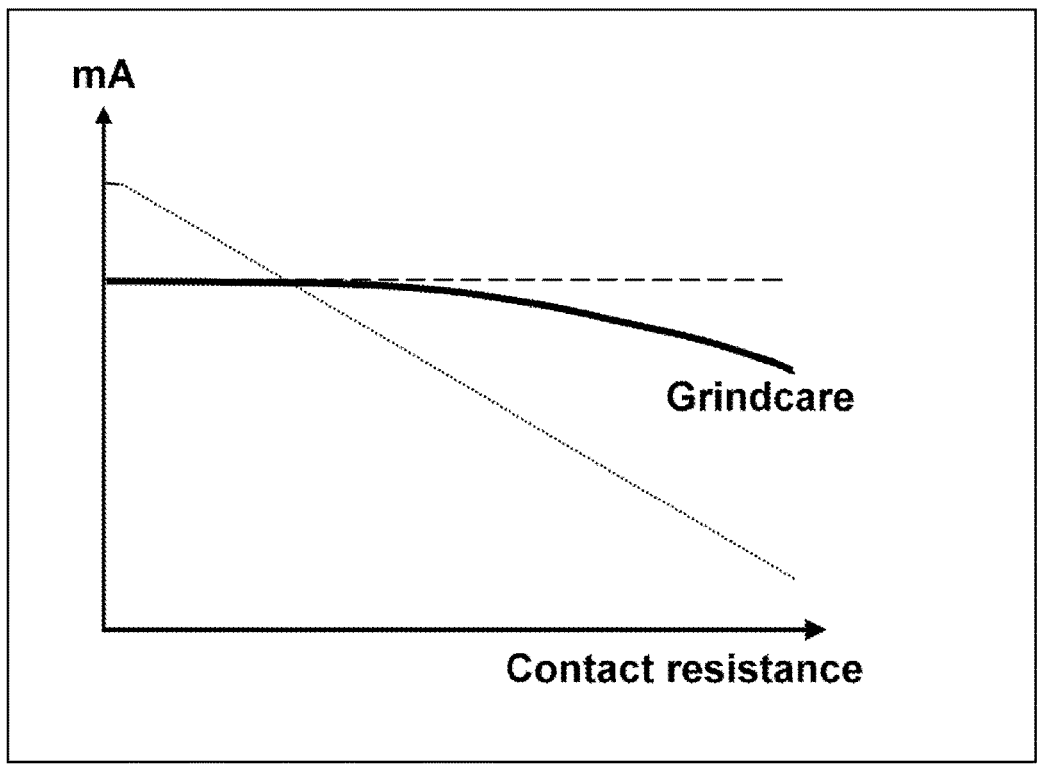
FIG. 1 show the difference in applied current between a current controlled and a voltage controlled apparatus
Figure 2:
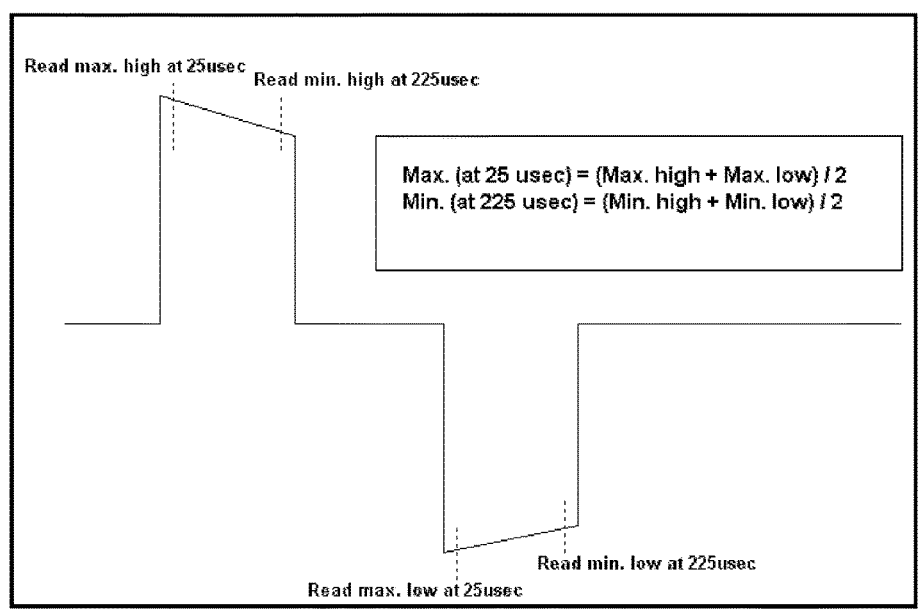
FIG. 2 is an illustration of a pulse cycle
Figure 3:
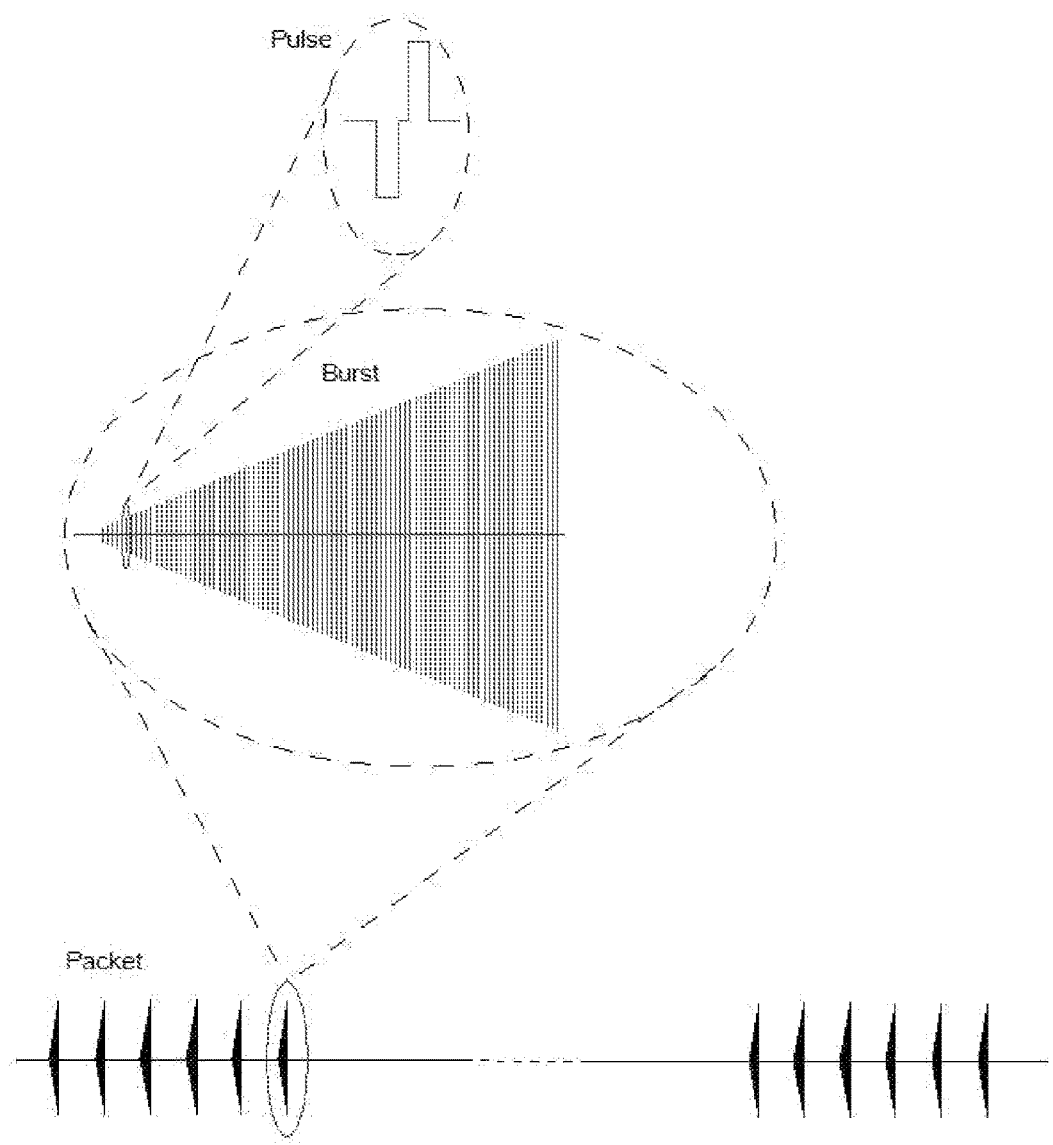
FIG. 3 shows the relation between pulse, packets and periods
Figure 4:
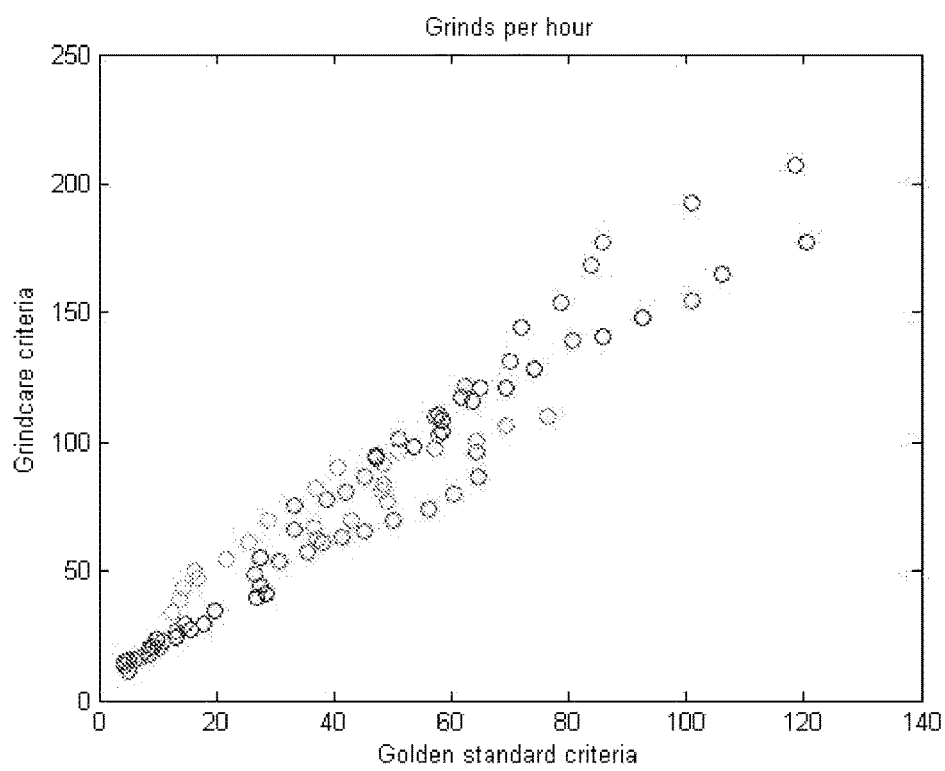
FIG. 4 shows the concordance between grinds per hour when detected by an apparatus according to the invention and the Golden Standard criteria

FIG. 4 shows the concordance between grinds per hour detected by the apparatus according to the invention and the golden standard, and it is seen that the detected grinds by apparatus according to the invention correlate well to the grinds detected by the golden standard.

Example 2—Impact of Bruxism

Figure 5:
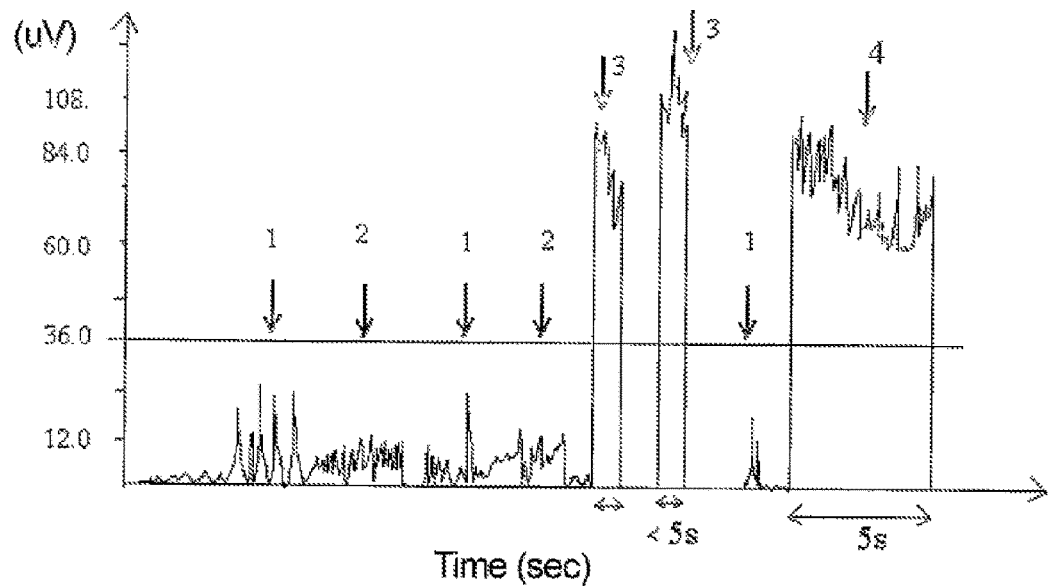
FIG. 5 shows muscle activity vs. time registered by an electrode assembly
Figure 6:
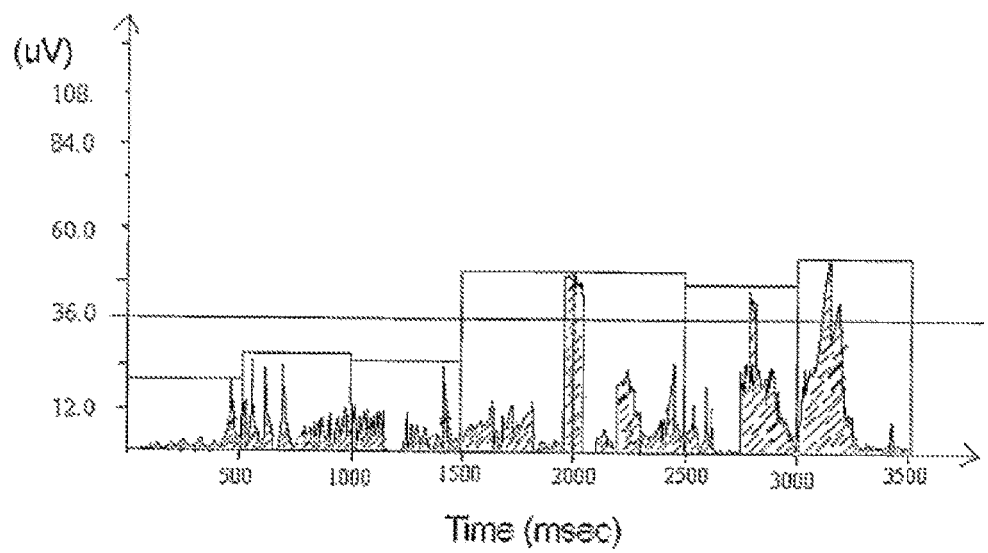
FIG. 6 illustrates an integration of muscle activity vs. time

FIG. 5 shows the amplitude (in µV) of the muscle activity signal vs. time. A threshold at 36 µV has been indicated with a horizontal line. Only the muscle activity events labelled "3" and "4" are above the threshold. FIG. 6 illustrates integration of the muscle activity vs. time diagram, i.e. the area under the curve has been determined to determine the impact of the measured muscle activity. The integration is provided for the entire curve, i.e. the amplitude of the muscle activity does not need to pass a certain threshold to become part of the integration.

Figure 7:
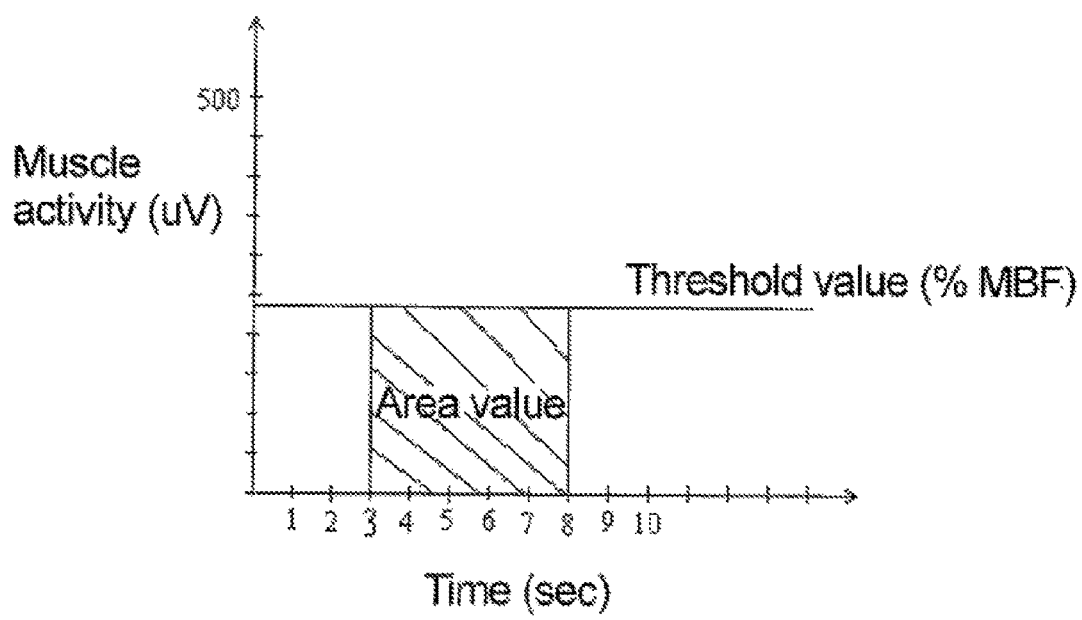
FIG. 7 illustrates integration of a bruxism event
Figure 8:
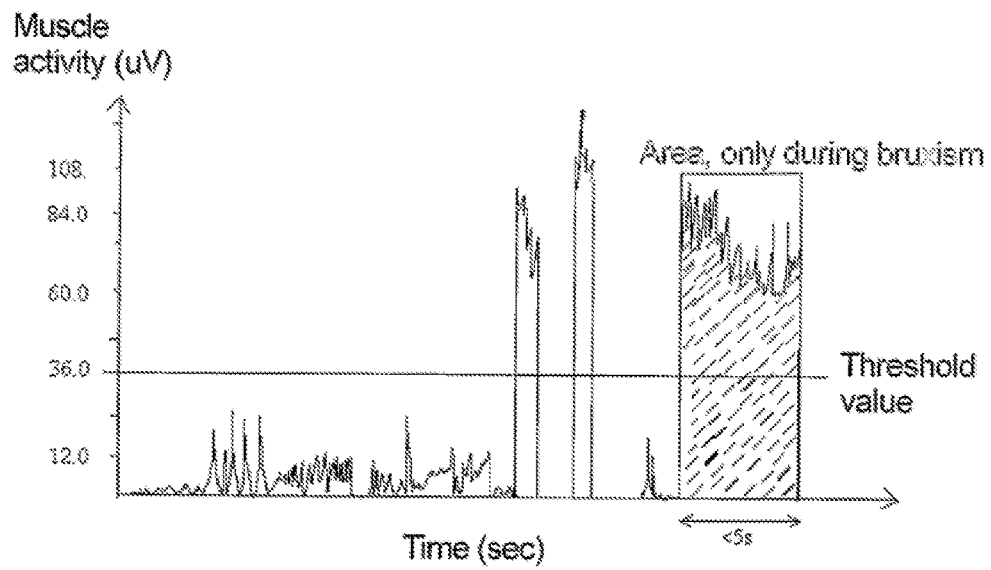
FIG. 8 illustrates an example of a threshold.
Figure 9:
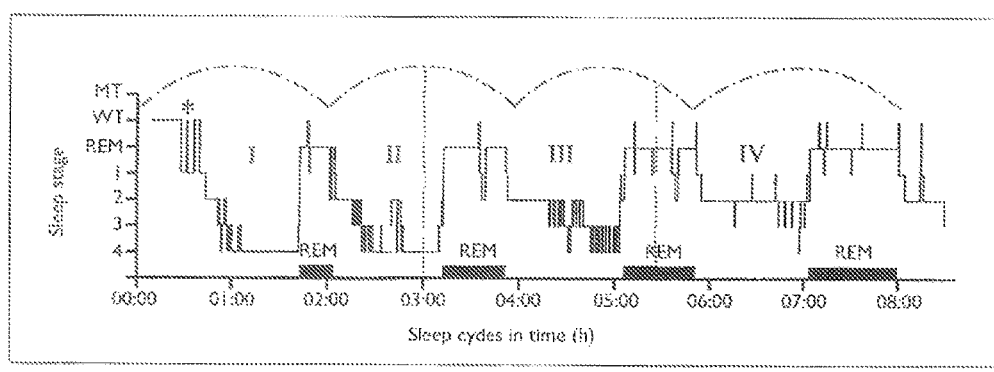
FIG. 9 shows sleep cycles during an 8 hours sleep
Figure 10:
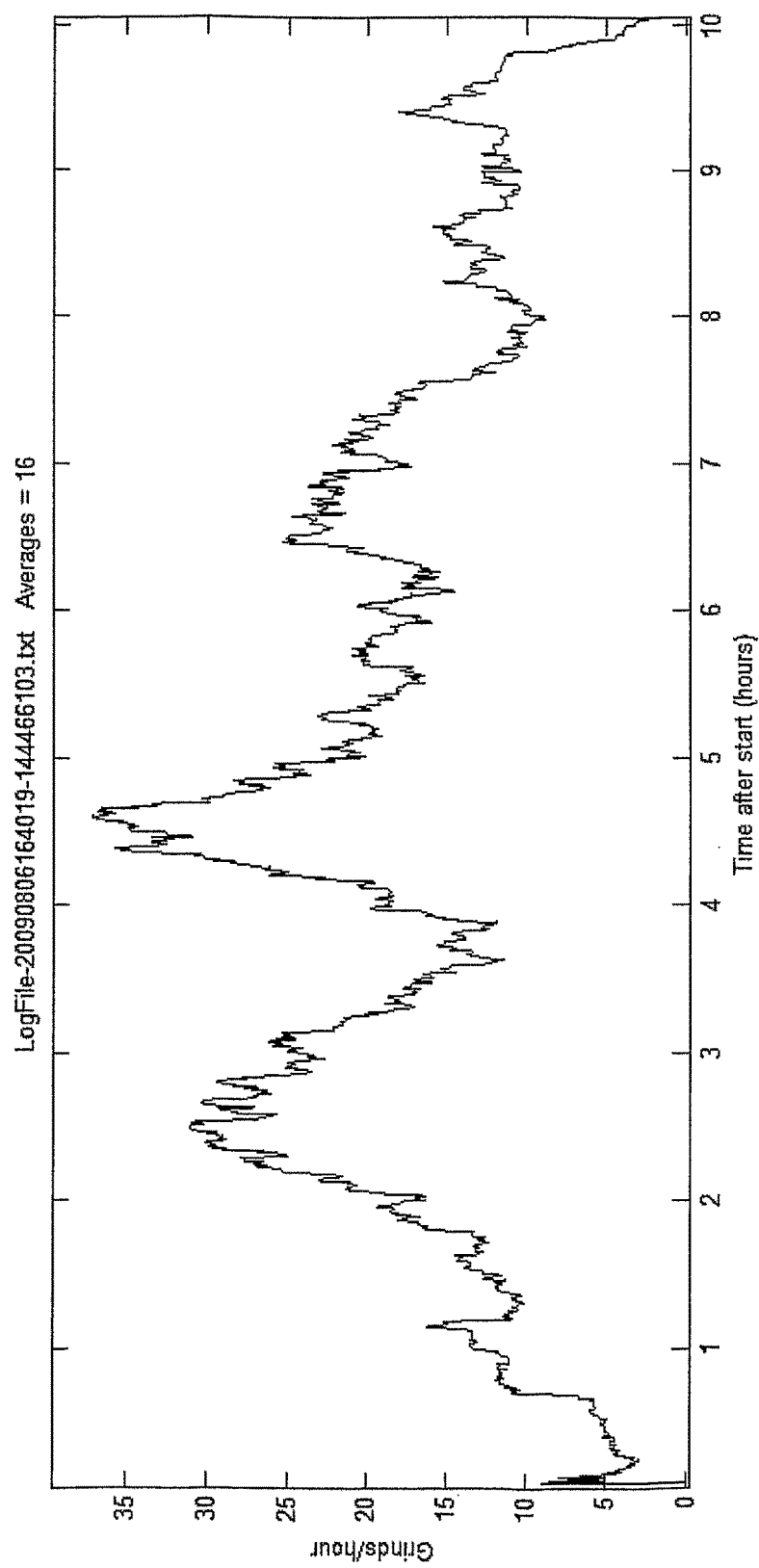
FIG. 10 shows grinds per hour detected during sleep

FIG. 7 illustrates an example of a threshold defined by means of both amplitude and time, i.e. an area under curve threshold. To surpass the threshold muscle activity must be above a certain amplitude for a certain amount of time. FIG. 8 illustrates an integration of the event in FIG. 5 labelled "4". This event is the only surpassing the threshold indicated in FIG. 7.

Example 3—Two Case Stories

Two individuals suffering from bruxism were studied for the long term effect (about 1-1½ month) of electrical stimulation using a feedback apparatus according to the invention during sleep.

The results show that the impact of bruxism is multidimensional and thereby that relief of type of symptoms may vary from individual to individual.

Figure 11A:
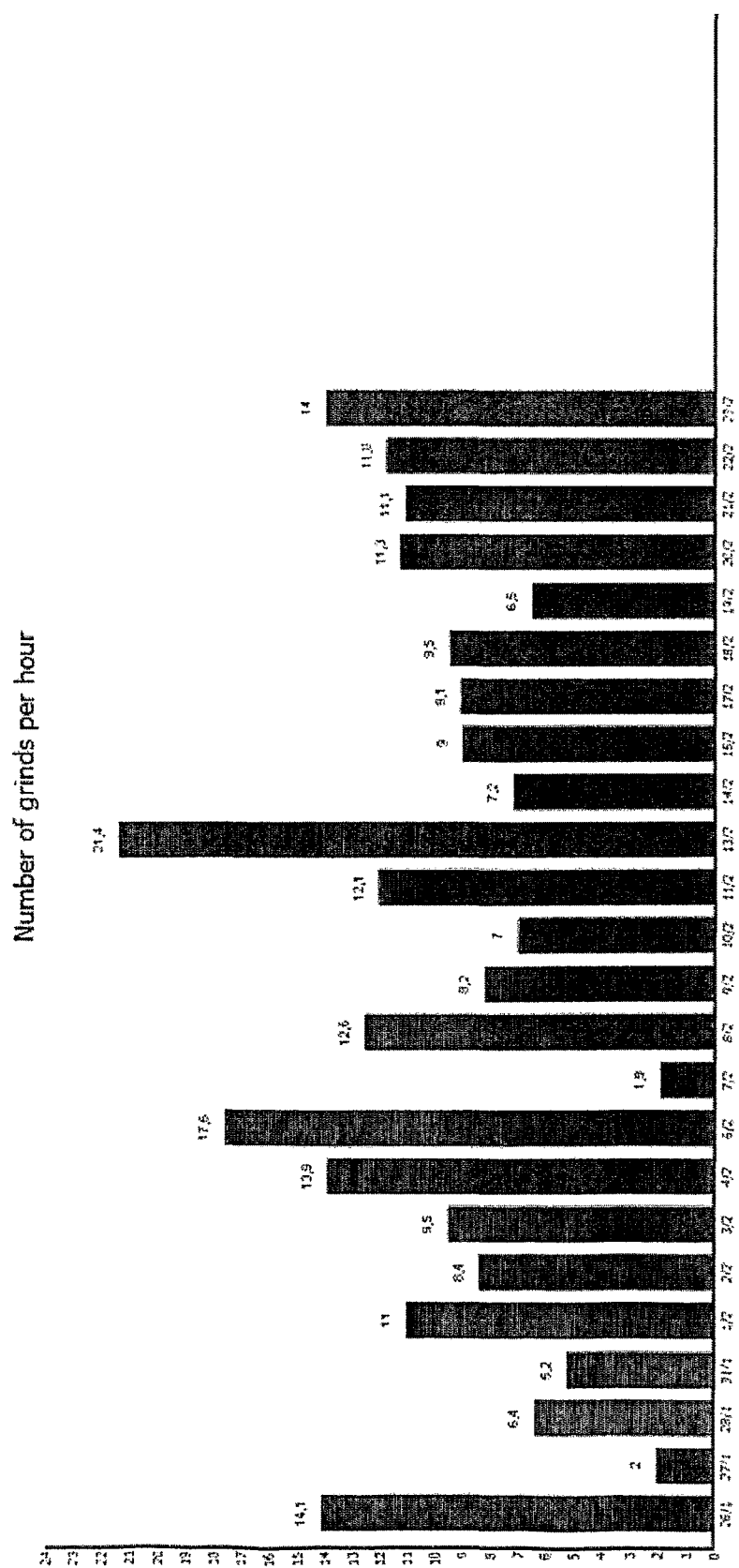
FIGS. 11a and 11b shows grinds per hour for two individuals going through treatment using an apparatus according to the invention

FIG. 11a shows the results from an individual receiving biofeedback at level 3 for all nights except for 1 night where the individual received biofeedback at level 4. The number of grinds are seen to vary over the period observed. However, the individual felt a significant decrease in the pain felt, and consequently felt a relief over the treatment although the number of bruxism events not significantly decreased, most probably due to less intensity of the bruxism events.

Figure 11B:
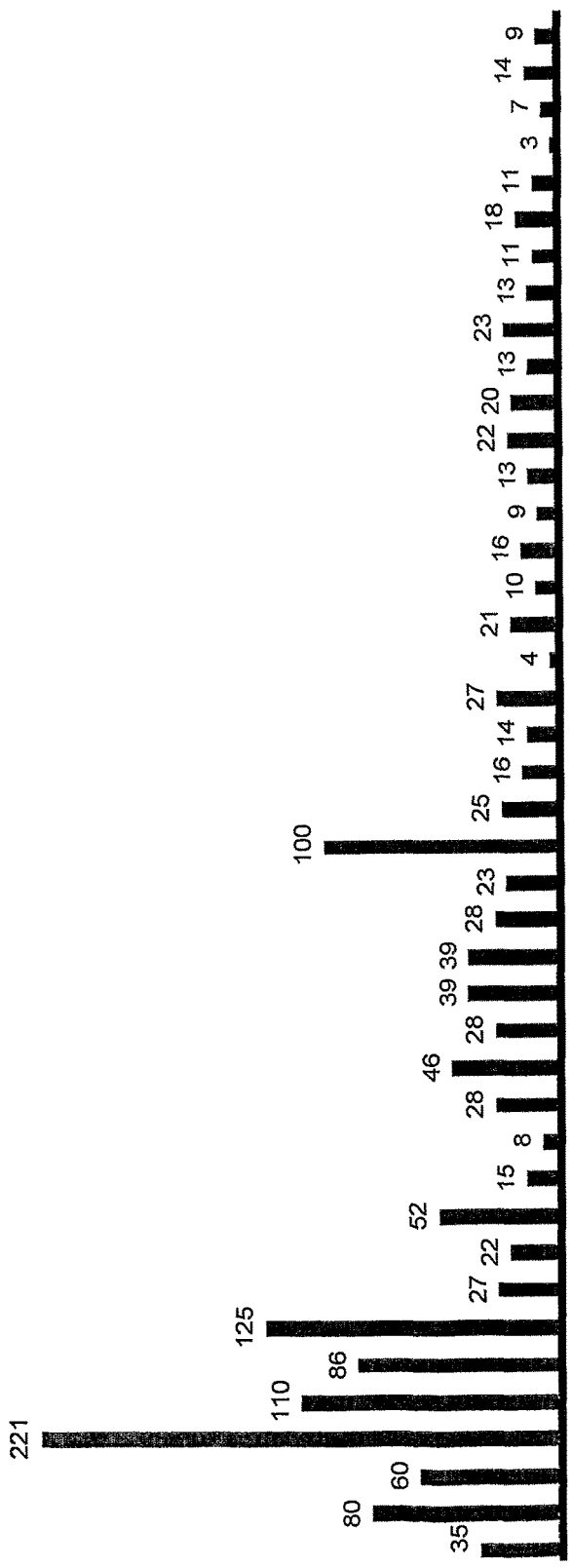

FIG. 11b shows the results from an individual receiving biofeedback at level 3-5. For the first 7 days only baseline measurements were determined without any biofeedback, and then from day 8 biofeedback commenced and continued for the remaining period. The number of grinds is seen to decrease significantly during the treatment period. Furthermore, the individual also felt a significant decrease in pain.

Example 4—Stimulus Signals Having No Impact on Sleep

Fourteen individuals suffering from bruxism (mean age: 32 years, 10 women, 4 men) were included in the study. All individuals were subjected to a polysomnographic study (PSG) designed to investigate the effect of electrical stimulation on PSG parameter, and thereby indirectly investigate whether the electrical stimulation did evoke cortical responses. The PSG parameters included: EEG, EMG, heart rate, sleep and respiratory parameters in order to score sleep pertubations such as arousals, awakening and shifts in sleep stage.

All individuals underwent a full PSG in the laboratory for three consecutive nights, one night for baseline recordings, one night without and one night with electrical stimulation. Electrical stimulation was conducted by a feedback apparatus according to the invention providing a stimulus as a feedback to a bruxism event. The stimulation was an electrical square-wave pulse train (450 ms) adjusted to a clear intensity (1-9 mA) through the electrodes applied if jaw clenching or grinding activity was detected.

The total sleep time, number of micro-arousals/hour sleep, the time (in minutes and in percent of total sleep time) spent in sleep stages 3 and 4, REM sleep, and number of periodic limb movements were not influenced by the electrical stimulation.

It may therefore be concluded that electrical stimulation does not cause arousal and disruption in sleep and therefore does not affect the overall quality of sleep.

Example 5—Stimulation of Reflex 11 individuals volunteered in the trial, wherein data was recorded during stimulation. The individuals were asked to bite on a force transducer to 10%, 20%, 30%, 40% and 50% of their maximum bite force and keep it constant for 20 seconds, using the visual feedback from the force transducer as a guide. During each recording, biofeedback stimulus pulse trains were issued by the feedback apparatus according to the invention. This was done manually by the experimenter, using the setup-menu on the apparatus. Each time stimulus level started with 0 and going through all steps up to level 6 or 7.

It was then examined whether the biofeedback has any effect on the EMG and consequently on the bite force.

Figure 12A:
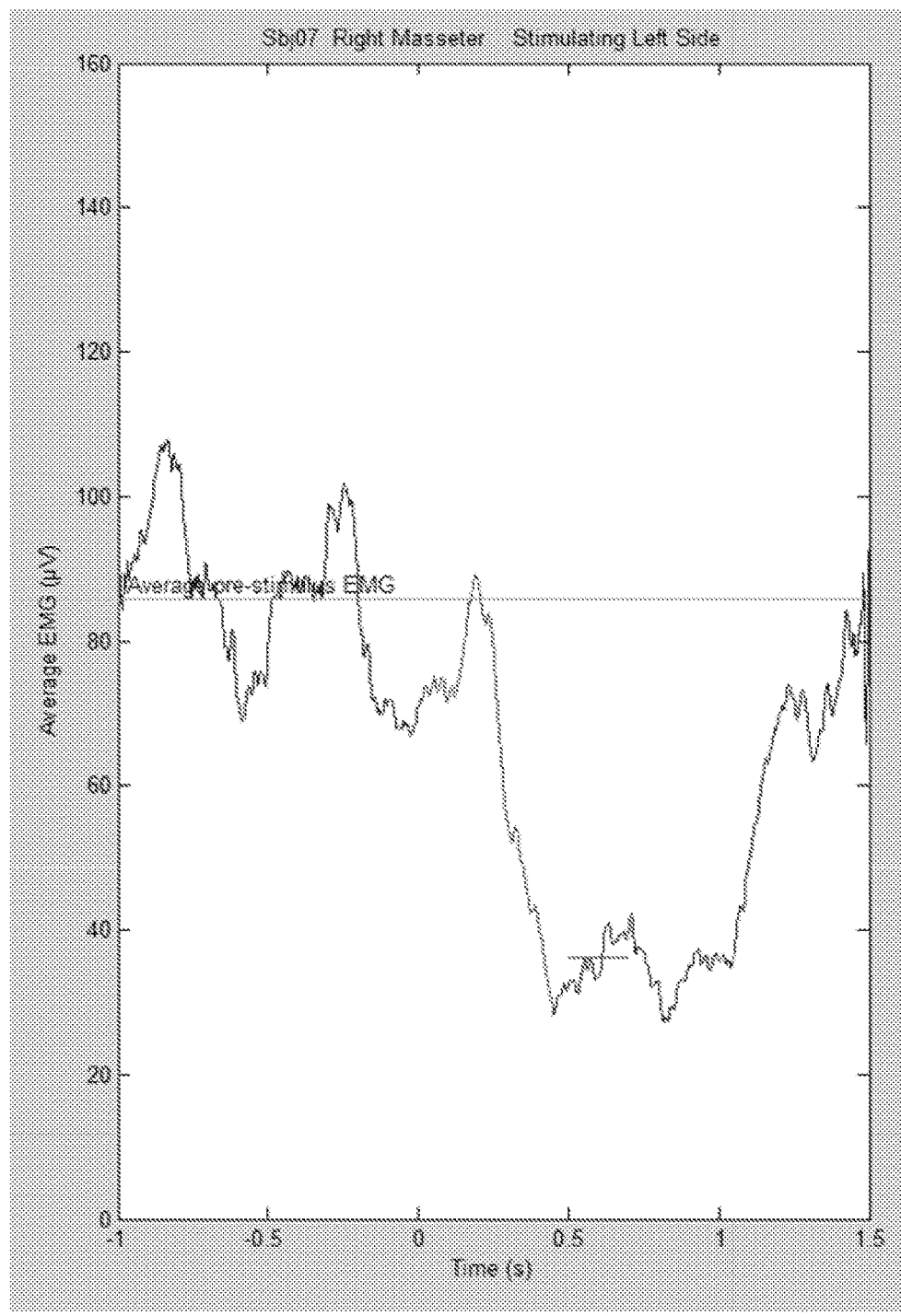
FIGS. 12a and 12b show effect of stimulus on EMG and bite force, respectively
Figure 12B:
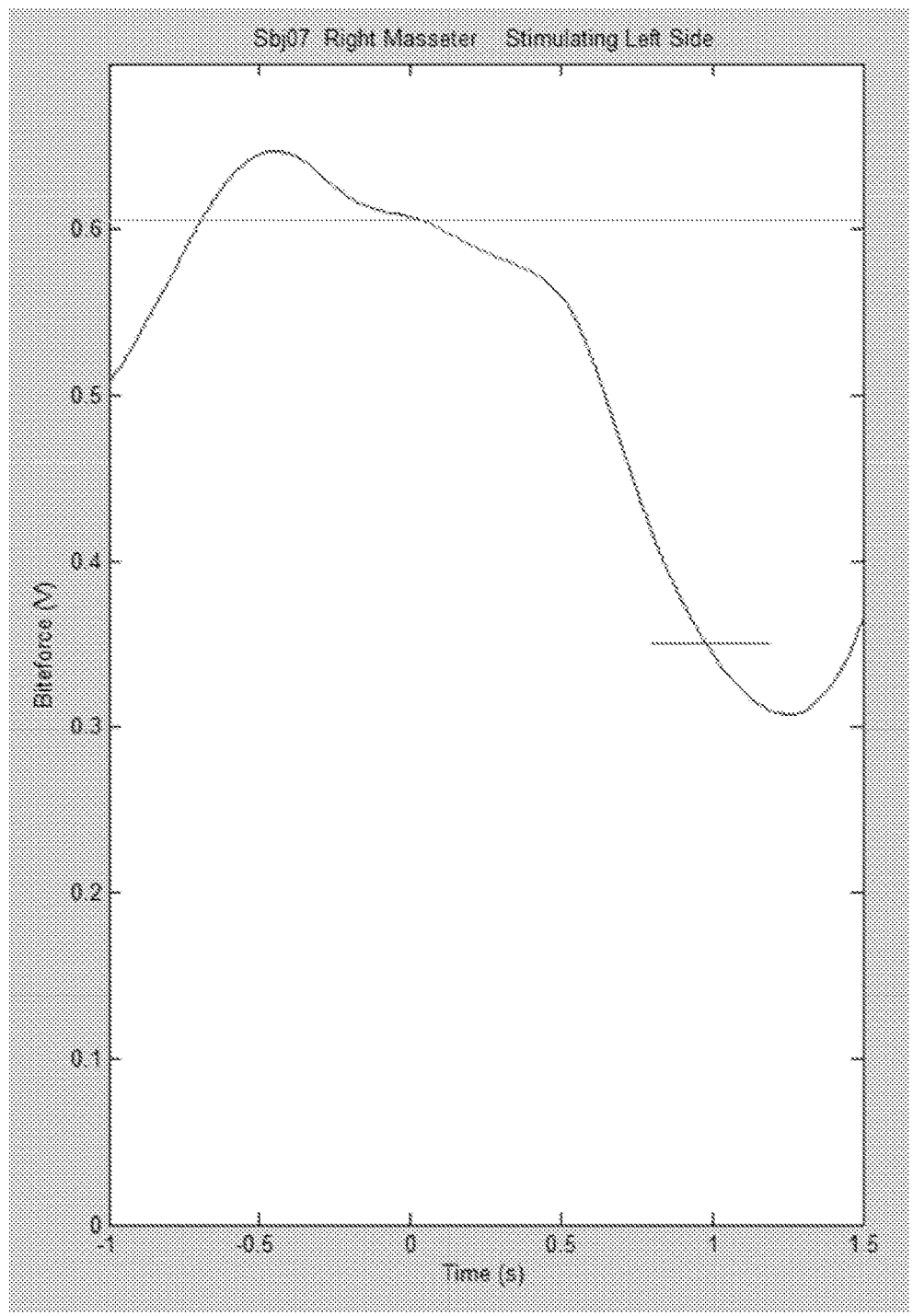

The data shown in FIGS. 12a and 12b indicates that there is a clear effect of the stimulation on the EMG and the bite force, since the EMG (FIG. 12a) shows a clear decrease within few hundred milliseconds from the stimulus, and the bite force (FIG. 12b) correspondingly is shown to decline after stimulation. Please note that the decrease in EMG is found on the site not being directly stimulated.

This indicates that an inhibitory reflex has been induced resulting in relaxation of the jaw muscles.

Example 6—Apparatus According to the Invention

Figure 13:
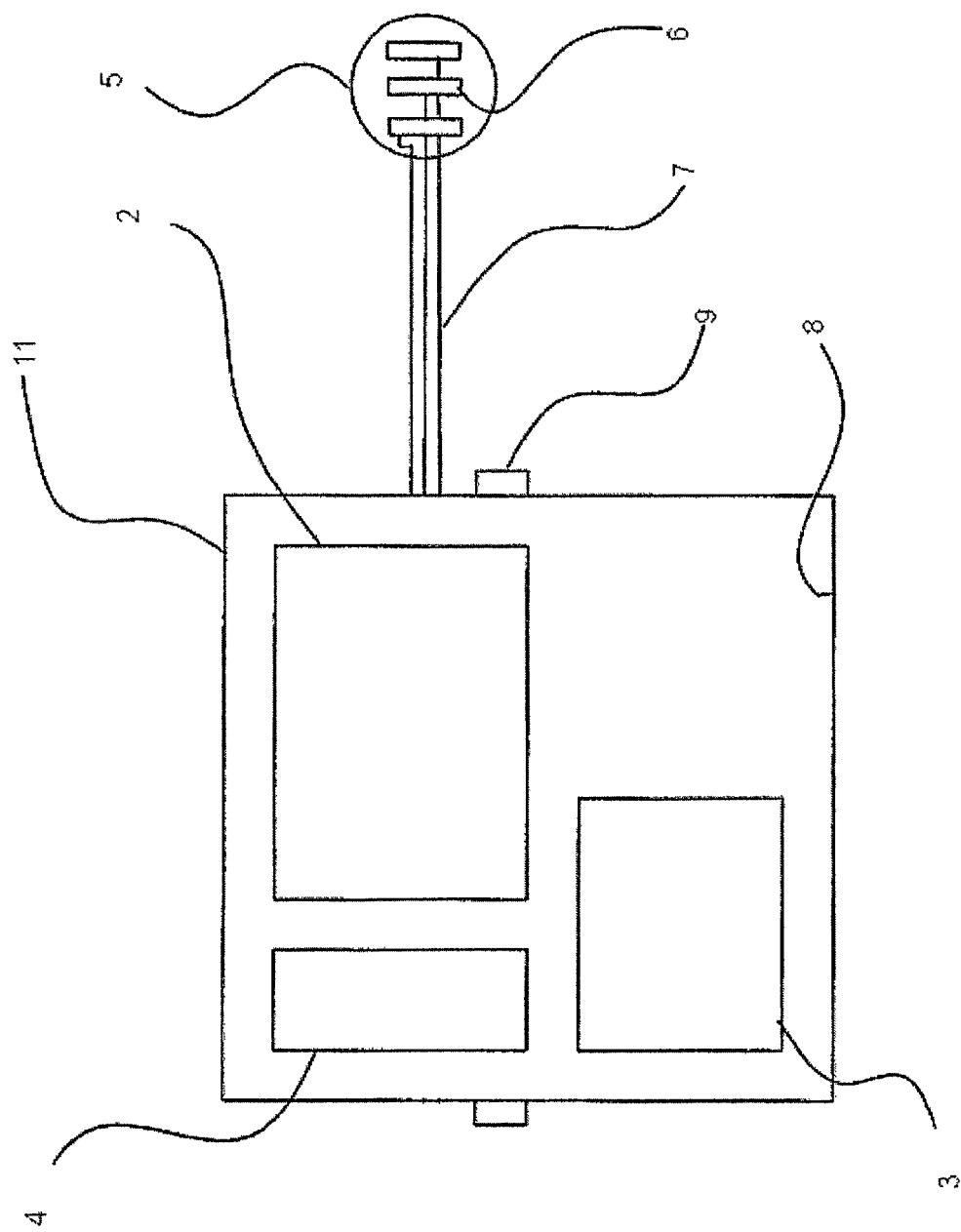
FIG. 13 is a general overview of an apparatus according to the invention

In FIG. 13 a general overview of an apparatus according to the invention has been shown in block diagram for showing the main components of such an apparatus. Thus, the housing 1 is illustrated comprising a processor 2 for processing signals, storing settings, data etc and facilitating transmission of biofeedback signals etc. Further, the housing 1 comprises the main display means 3 and an energy supply source in the form of a battery 4. The housing 1 may have one or more buttons or keys 9 as well as a plug-in connector 8, eg. a USB connector or the like. This connector 8 may be connected to a PC or the like by means of a connector plug, eg. for setting up the apparatus or for transmitting data to the PC, from which it may be transmitted to a supervisor, eg. a dentist or a medically trained person. Further, the same connector 8 may facilitate a charging of the battery 4.

Further, it is shown in FIG. 13 that an electrode assembly 5 comprising a number of electrodes 6 is connected to the apparatus by means of wires 7.

In the aspects wherein stimulation signals are applied randomly then the processor 2 facilitates the stimulation signals, whereas biofeedback signals are only facilitated in combination apparatuses. For both the simple random apparatus as well as the combination apparatus detecting of bruxism events may still be relevant for monitoring causes.

The invention claimed is:

1. A method for preventing bruxism of an individual in a period of time by application of electric stimuli in a randomly selected frequency, comprising the steps of:
   a. attaching at least one electrode assembly to the skin of the individual in a region effective to treat bruxism before occurrence of bruxism;
   b. providing an electric stimulus by a processing control unit as a packet, the packet having a pulse train with predefined parameters including: start current, end current, start voltage, end voltage, pulse width, pulse train duration, inter-pulse spacing, duty cycle of each pulse, and pulse set spacing;
   c. applying the electric stimulus to the region by the at least one electrode assembly attached to the skin of the individual for relaxation of at least one of a masticatory and/or facial muscles of the individual, wherein the processing control unit is not processing monitoring signals;
   d. randomly selecting by the processing control unit a packet frequency between 0.001 and 1 Hz, where the packet frequency is defined as a rate of packets during the period of time, where a time duration between two packets in the period of time defines an inter-packet interval;
   e. at an end of the inter-packet interval, providing the electric stimulus with the predefined parameters in b and repeating c; and
   f. repeating d and e until the period of time ends;
   whereby the electric stimuli are provided to the individual where the processing control unit is not processing monitoring signals during the period of time, such that the application of the electric stimulus results in relaxation of at least one of the masticatory and/or facial muscles of the individual, thereby preventing the bruxism before occurrence of the bruxism.

2. The method according to claim 1, wherein the duration between two subsequent electric stimuli is selected randomly between 1 and 10 seconds, or between 10 and 100 seconds or between 100 and 1000 seconds.

3. The method according to claim 1, wherein each electric stimulus has a current of at least 0.5 mA, or at least 2.0 mA, or at least 10.0 mA, or at least 20.0 mA.

4. The method according to claim 1, wherein each pulse train comprises at least 5 pulses, or least 10 pulses, or at least 50 pulses.

5. The method according to claim 1, wherein the duration of each pulse train is at least 10 milliseconds, or at least 50 milliseconds, or at least 100 milliseconds, or at least 400 milliseconds.

6. The method according to claim 1, wherein an intensity of the pulse is increased during each pulse train.

7. The method according to claim 1, wherein an intensity of the pulse decreases towards the end of each pulse train.

8. The method according to claim 1, wherein the duration of each pulse is at least 50 microseconds, or at least 100 microseconds, or at least 200 microseconds.

9. The method according to claim 1, wherein said period of time is a predefined period of time during night time.

10. The method according to claim 1, wherein said period of time is a predefined period of time during a predefined sleep cycle of the individual.

11. The method according to claim 1, wherein a setting of the electric stimulus is selected to be sufficient for inducing an exteroceptive suppression period for the muscle(s) involved in bruxism.

12. The method according to claim 1, wherein the frequency and/or an intensity of the applied stimulation signals are adjusted in response to intensity, impact, frequency and/or duration of detected bruxism episodes.

13. The method according to claim 1, for treatment of one or more of the following disorders: bruxism, awake bruxism, chronic bruxism, night time bruxism, dental wear, temporal mandibular joint disease (TMJ), tinnitus, migraine, headache, tension headache.

14. An apparatus for preventing bruxism of an individual, comprising:
  a housing;
  the at least one electrode assembly accommodated in the housing and configured to be attached to the skin of the individual, the at least one electrode configured to apply a plurality of electrical stimulation signals to at least one of the masticatory and/or facial muscles of said individual for providing relaxation of said muscle(s);
  the processing control unit;
  a main terminal interface; and
  an energy supply source for applying energy to the electrode assembly and the processing control unit,
  wherein the processing control unit is configured to carry out the method of claim 1.

15. An apparatus according to claim 14, wherein an electrical stimulation signal is a pulse train with a one or more of the following parameters being predefined: start current, end current, start voltage, end voltage, pulse width, pulse train duration, inter-pulse spacing, duty cycle (pulse), pulse set spacing, duty cycle (pulse set).

16. An apparatus according to claim 14,
  wherein said housing having outer dimensions of:
  length less than 50 mm, or less than 20 mm,
  width less than 40 mm, or less than 10 mm, and
  height less than 20 mm, or less than 10 mm, or less than 2 mm.

* * * * *